(12) United States Patent
Ahmad et al.

(10) Patent No.: US 12,139,413 B2
(45) Date of Patent: Nov. 12, 2024

(54) METHOD FOR GENERATING A GAS-PRODUCT

(71) Applicant: Siemens Energy Global GmbH & Co. KG, Bayern (DE)

(72) Inventors: Suhel Ahmad, Duisburg (DE); Thomas Mönk, Gladbeck (DE)

(73) Assignee: Siemens Energy Global GmbH & Co. KG, Munich (DE)

( * ) Notice: Subject to any disclaimer, the term of this patent is extended or adjusted under 35 U.S.C. 154(b) by 637 days.

(21) Appl. No.: 17/437,562

(22) PCT Filed: Feb. 28, 2020

(86) PCT No.: PCT/EP2020/055264
§ 371 (c)(1),
(2) Date: Sep. 9, 2021

(87) PCT Pub. No.: WO2020/193071
PCT Pub. Date: Oct. 1, 2020

(65) Prior Publication Data
US 2022/0135414 A1 May 5, 2022

(30) Foreign Application Priority Data
Mar. 27, 2019 (EP) .................................... 19165464

(51) Int. Cl.
| C01C 1/04 | (2006.01) |
| C01B 3/34 | (2006.01) |
| C07C 5/327 | (2006.01) |
| F04D 17/10 | (2006.01) |
| F04D 21/00 | (2006.01) |

(52) U.S. Cl.
CPC .................. *C01C 1/04* (2013.01); *C01B 3/34* (2013.01); *C07C 5/327* (2013.01); *F04D 17/10* (2013.01); *F04D 21/00* (2013.01); *C01B 2203/0216* (2013.01); *C01B 2203/0465* (2013.01); *C01B 2203/0495* (2013.01); *C01B 2203/068* (2013.01); *C01B 2203/0833* (2013.01)

(58) Field of Classification Search
CPC .. C01C 1/04; C07C 5/327; C01B 3/34; F04D 17/10; F04D 21/00
See application file for complete search history.

(56) References Cited

U.S. PATENT DOCUMENTS

| 2,949,224 | A | | 8/1960 | Pavlecka |
| 6,085,512 | A | * | 7/2000 | Agee .................... F02C 9/18 60/39.12 |
| 8,722,010 | B1 | | 5/2014 | Grover |
| 9,254,472 | B2 | | 2/2016 | Tang |
| 2008/0207975 | A1 | | 8/2008 | Crone et al. |
| 2009/0186952 | A1 | | 7/2009 | Steynberg et al. |
| 2009/0196731 | A1 | | 8/2009 | Lawlor |
| 2012/0020841 | A1 | | 1/2012 | Bushuev |
| 2013/0048916 | A1 | | 2/2013 | Ljunggren |
| 2013/0149100 | A1 | | 6/2013 | Lawlor |
| 2013/0223975 | A1 | | 8/2013 | Lawlor |
| 2014/0058149 | A1 | | 2/2014 | Negiz |
| 2014/0121346 | A1 | | 5/2014 | Tang |
| 2014/0243569 | A1 | | 8/2014 | Seppala et al. |
| 2016/0281722 | A1 | | 9/2016 | Byron et al. |
| 2017/0350318 | A1 | | 12/2017 | Williams et al. |
| 2020/0039831 | A1 | | 2/2020 | Gorval et al. |

FOREIGN PATENT DOCUMENTS

| CN | 101918719 A | 12/2010 |
| CN | 102427875 A | 4/2012 |
| CN | 102865140 A | 1/2013 |
| CN | 102985516 A | 3/2013 |
| CN | 104540583 A | 4/2015 |
| CN | 104853838 A | 8/2015 |
| CN | 104854021 A | 8/2015 |
| CN | 106687207 A | 5/2017 |
| CN | 107476884 A | 12/2017 |
| CN | 107543679 A | 1/2018 |
| CN | 109053574 A | 12/2018 |
| DE | 102015210801 A1 | 12/2016 |
| RU | 2412226 C2 | 2/2011 |
| WO | 2013009644 A2 | 1/2013 |
| WO | 2014070419 A2 | 5/2014 |
| WO | 2016001476 A1 | 1/2016 |

OTHER PUBLICATIONS

PCT International Search Report and Written Opinion of International Searching Authority mailed Jul. 13, 2020 corresponding to PCT International Application No. PCT/EP2010/055264 filed Feb. 28, 2020.

* cited by examiner

Primary Examiner — Yong L Chu
(74) Attorney, Agent, or Firm — Wolter Van Dyke Davis, PLLC

(57) ABSTRACT

A method for generating a gas-product includes: a) providing a first part of a feed stream; b) providing a second part of a feed stream; c) combining the first part of the feed stream with the second part of the feed stream into the feed stream; d) heating at least one of: the first part of the feed stream, the second part of the feed stream before step c, the feed stream after step c; e) conducting the feed stream into a reactor; f) reacting the feed stream into the gas-product. To reduce investment and in particular the footprint of the machine step d) is at least partly performed by compressing the respective stream by a supersonic compressor such that the respective stream is heated.

10 Claims, 5 Drawing Sheets

METHOD FOR GENERATING A GAS-PRODUCT

CROSS REFERENCE TO RELATED APPLICATIONS

This application is the US National Stage of International Application No. PCT/EP2020/055264 filed 28 Feb. 2020, and claims the benefit thereof. The International Application claims the benefit of European Application No. EP19165464 filed 27 Mar. 2019. All of the applications are incorporated by reference herein in their entirety.

FIELD OF INVENTION

The invention relates to a method for generating a gas-product.

BACKGROUND OF INVENTION

In the terminology of the invention a supersonic compressor is a compressor comprising a rotor wherein at least one part of the rotor reaches Mach 1 respectively at least sonic velocity regarding the local process fluid condition during standard operation of the respective compressor.

One example of a supersonic compressor is shown in US 2016/0281722 A1.

According to the terminology of the invention synthesis gas or syngas, is a gas-mixture used as intermediate to generate a gas-product—like syngas, hydrogen or ammonia. Syngas consists primarily of hydrogen, carbon monoxide, and very often some carbon dioxide.

Syngas can be produced from many sources, including natural gas, coal, biomass, or virtually any hydrocarbon feedstock, by reaction with steam (steam reforming), carbon dioxide (dry reforming) or oxygen (partial oxidation).

For the production of synthesis gas mostly steam methane reforming process is used. The reaction is endodermic so external heat sources must be provided to the system. Conventionally the external heat is supplied by a furnace. Additionally, the reaction needs a pressure of 20 bar-30 bar to generate the desired gas product.

The furnace requires a significant amount of energy during the operation and providing the furnace is costly as well as the maintenance.

Another example of a large-scale product gas generation is the propane dehydrogenation process. During this process propylene is produced from propane by removing hydrogen. This reaction takes place in a reactor in presence of a catalyst. One feed gas stream propane is heated at a high temperature in a furnace and fed to the catalytic reactor to be converted into the product gas propylene. The catalyst needs continuous regeneration by supplying air into the reactor.

Another example of a large-scale gas product generation is the production of ammonia. Conventionally such production plants require a costly furnace being able to operate under a high-pressure level.

SUMMARY OF INVENTION

It is one object of the invention to provide a gas product generation method with a reduced foot print and reduced investment and operation costs.

According to the invention the method of the incipiently mentioned type enables reduced investment and operation costs and in particular a smaller foot print of the arrangement.

One beneficial feature of the invention is that the supersonic compressor enables a significant increase in pressure and temperature with a significantly reduced foot print comparted to conventional arrangements.

A supersonic compression according to the invention is in particular beneficial for simultaneously increasing pressure and temperature of a gas feed stream enabling a subsequent reaction in a reactor without additional operation of a furnace.

In order to avoid a reaction outside of the reactor an embodiment provides that a first part of a feed stream for the reaction is heated by compressing by a supersonic compressor. Combining at least two or several parts of said feed stream downstream of the supersonic compression of at least one part of the feed stream avoids undesired reactions inside of a supersonic compressor during increase of pressure and temperature.

Another embodiment provides a heat exchange between a second part of said feed stream upstream of entering the reactor and the reactor itself or a gas product downstream of exiting the reactor.

Another beneficial option is given by driving said supersonic compressor with a gas turbine generating exhaust gas wherein said exhaust gas is used to heat said first part and/or second part of said feed stream. This way thermal efficiency of the arrangement respectively of the method can be improved.

One embodiment provides a method according to the invention wherein said first part of said feed stream essentially consists of hydrocarbon, said second part of said feed stream essentially consists of water and wherein the gas product essentially consists of syngas. Said syngas can be separated from water and from carbon oxide to obtain hydrogen downstream of the reactor which can be used for any subsequent process.

Another embodiment of the invention is given by said first part of said feed stream essentially consisting of air, said second part of said feed stream essentially consisting of propane and said gas product essentially consisting of propylene. This process is advantageously operated such that a first part of said feed stream is heated by compressing said air with a supersonic compressor.

To additionally increase thermal efficiency a second part of said feed stream can be heated upstream of entering the reactor by exchanging heat with said first part of said feed stream downstream of exiting said supersonic compressor.

Another embodiment provides that said first part of said feed stream essentially consists of syngas and said second part of said feed stream essentially consist of air and said gas product essentially consists of ammonia. The syngas being provided as said first part of said feed stream may be generated according to the previously mentioned method providing a first part of feed stream as hydrocarbon and a second part of said feed stream as water.

DETAILED DESCRIPTION OF INVENTION

Figure 1:
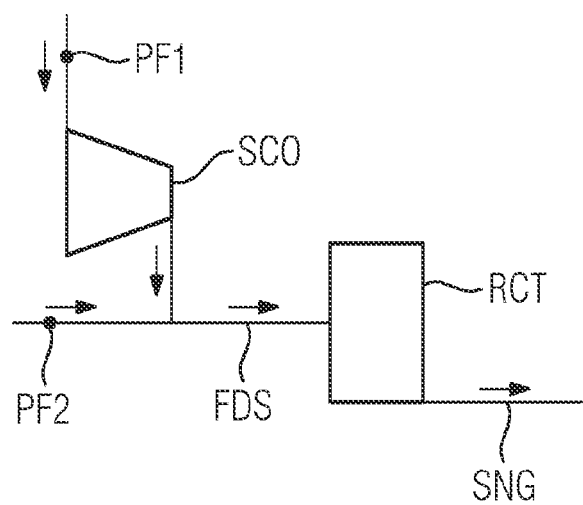
FIG. 1 shows a schematic flow diagram illustrating the basic principle of the method according to the invention, FIG. 2, 4, 5 respectively show a schematic flow diagram illustrating the principle of the method according to the invention applied to an ammonia synthesis.

FIG. 1 shows schematically a flow diagram illustrating the method generating a gas-product SNG according to the invention. In general, the method comprises the following steps:
a) providing a first part PF1 of a feed stream FDS,
b) providing a second part PF2 of a feed stream FDS,
c) combining said first part PF1 of said feed stream FDS with said second part PF2 of said feed stream FDS into said feed stream FDS,
d) heating at least one of
  i. said first part PF1 of said feed stream FDS,
  ii. said second part PF2 of said feed stream FDS before step c),
  iii. said feed stream FDS after step c),
e) conducting the feed stream FDS into a reactor,
f) reacting the feed stream FDS into the gas-product SNG.

According to the invention step d) is performed by compressing the respective stream FDS by a supersonic compressor SCO such that the respective stream is heated. The supersonic compressor SCO increases pressure and temperature according to the needs of the process in one step. This saves process equipment and therefore reduces investment costs and in particular machine footprint.

Figure 2:
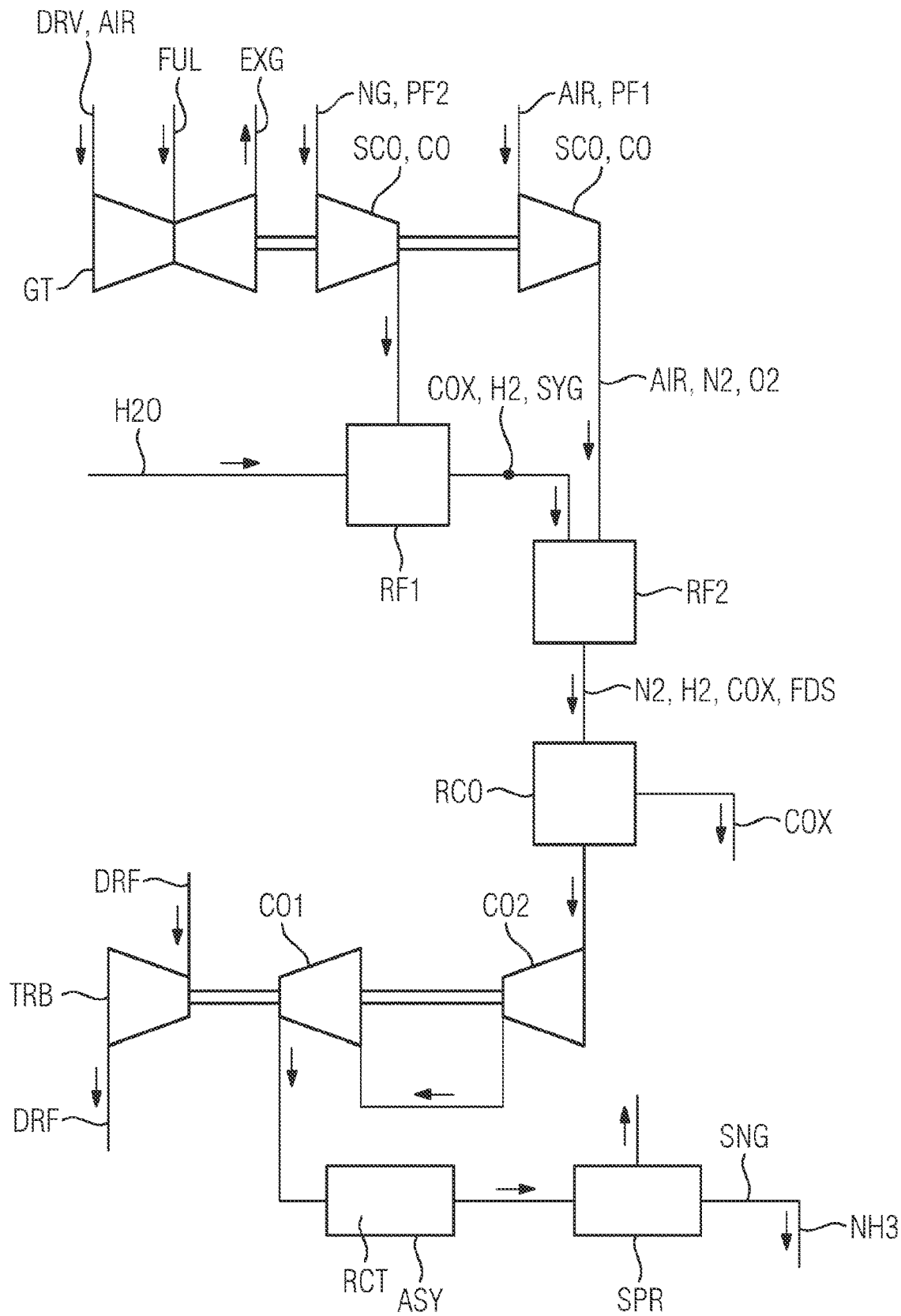
Figure 3:
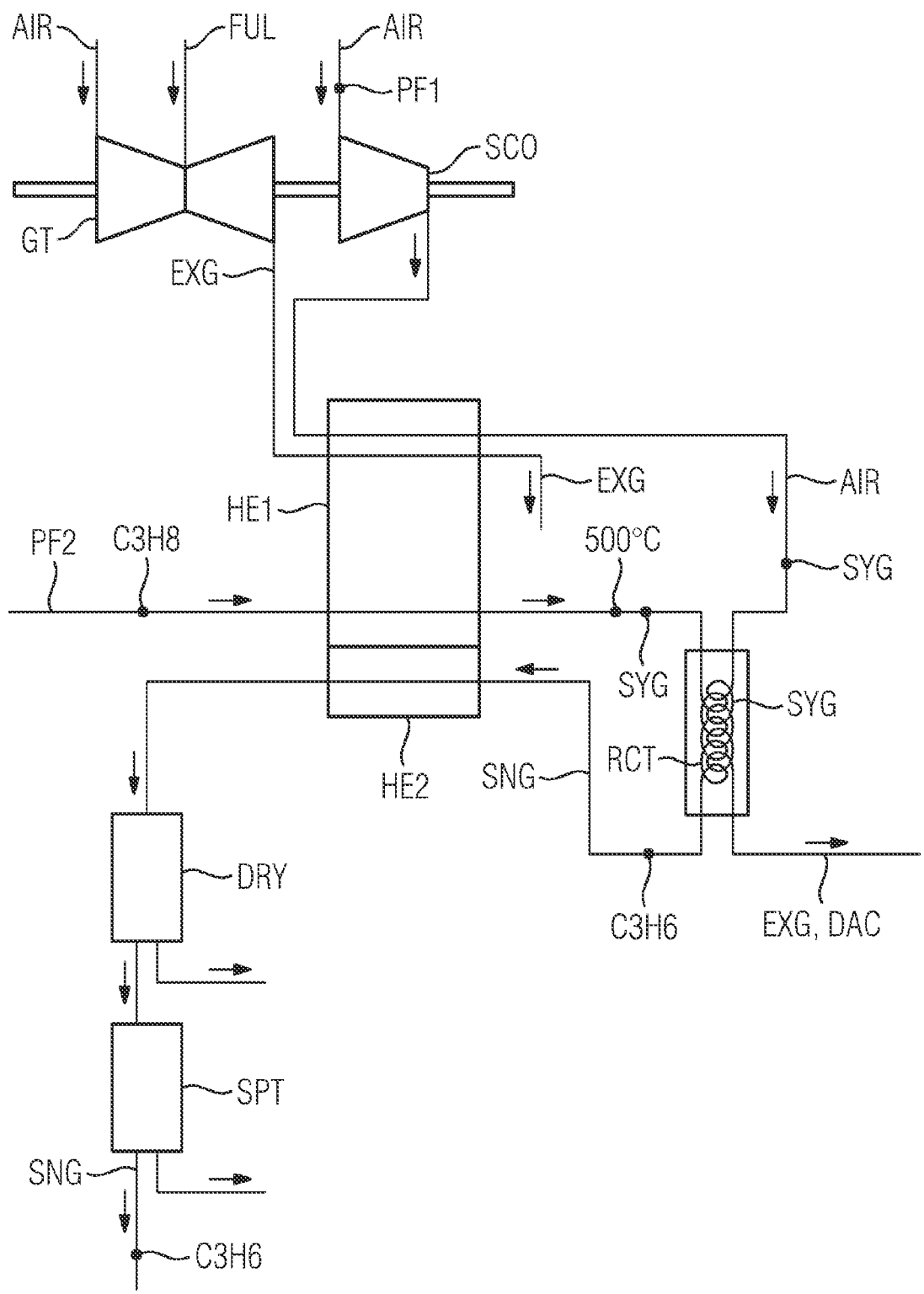
FIG. 3 shows a schematic flow diagram illustrating the basic principle of the method according to the invention applied to a propane dehydrogenation.

While FIG. 1 shows a general scheme of the invention illustrating the usage of the supersonic compressor SCO to obtain thermodynamic parameters needed by the process according to the method of the invention—FIGS. 2, 3 show more specific examples with more details. FIG. 2 shows a first variant to generate a gas-product SNG—here ammonia NH3. Input to the method—respectively the process is a first part PF1 of a feed stream FDS as air being compressed by a supersonic compressor or an ordinary compressor CO. A second part PF2 of a feed stream FDS is provided by natural gas NG which can be also compressed by a supersonic compressor SCO or an ordinary compressor CO. According to the invention at least one of the two parts PF1, PF2 of said feed stream FDS is compressed by a supersonic compressor SCO.

The illustration of FIG. 2 is meant to show that at least one of both compressors CO is provided as a supersonic compressor SCO. In this example both compressors CO, SCO are driven by a gas turbine GT being supplied with fuel FUL and air AIR. A drive DRV respectively the gas turbine GT generates an exhaust gas EXG which can be used in subsequent processes to heat other process fluids not illustrated in FIG. 2.

Downstream the compression of the natural gas NG, respectively the second part PF2 of the feed stream FDS is mixed with water H2O and reacted in a first reformer RF1 to obtain the syngas SYG. Said syngas SYG is a mixture basically of carbon oxide—in particular carbon monoxide—and hydrogen H2. The product of the first reformer RF1, respectively the syngas SYG is reacted in a second reformer with the compressed air, respectively the first part PF1 of the feed stream FDS containing nitrogen N2 and oxygen O2. The output of the second reformer basically is nitrogen N2, hydrogen H2 and carbon oxide COX being the feed stream FDS to be reacted in a reactor RCT downstream of a carbon oxide COX reduction module RCO. Additional compressors CO1, CO2 being driven by a turbine TRB are supplied with a driving fluid DRF wherein the reactor RCT completes the ammonia synthesis ASY. Downstream of the reactor RCT impurities are removed from the gas-product SNG in a separator SPR to obtain ammonia NH3.

Figure 4:
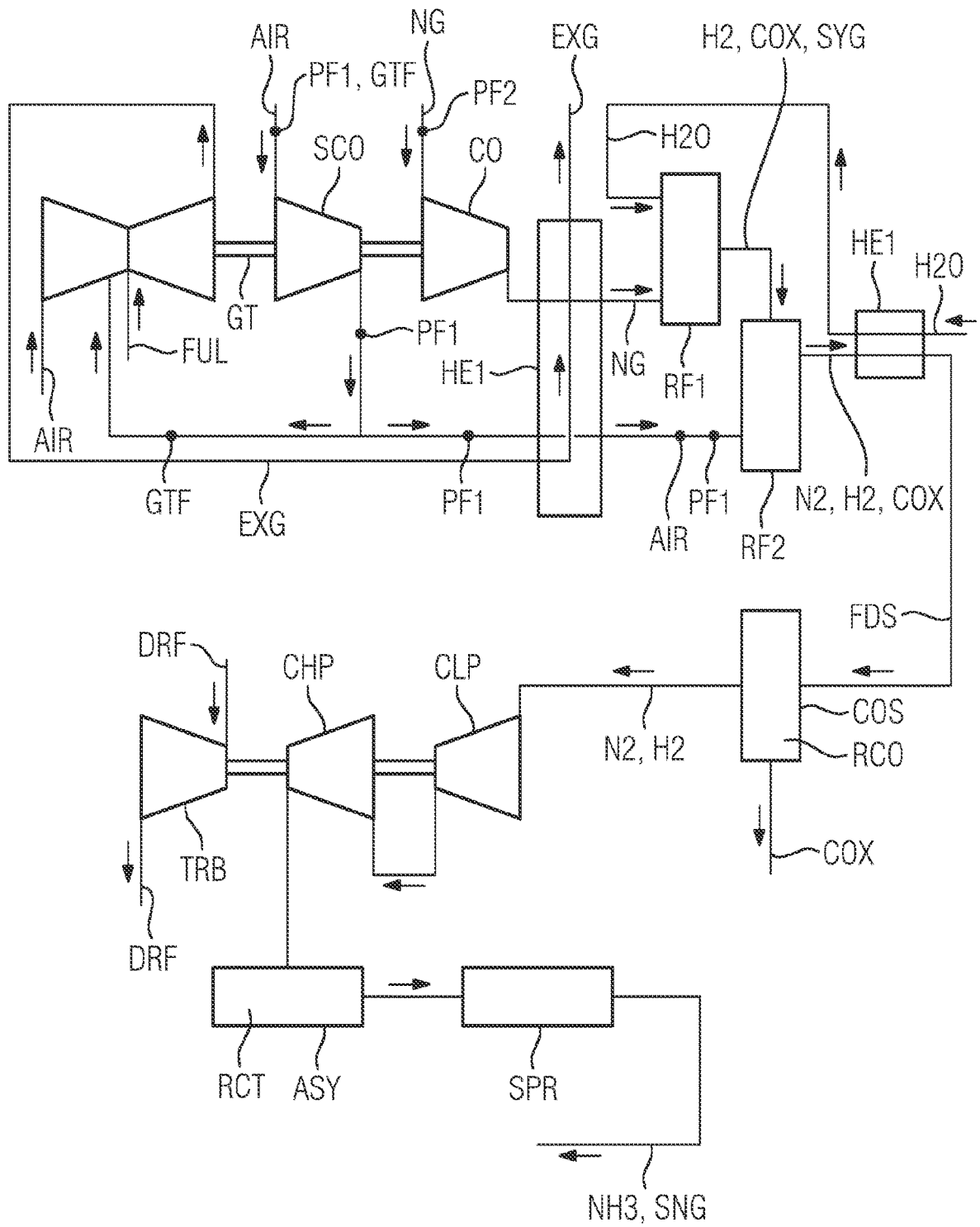

FIG. 4 basically shows a similar process with slight differences regarding the first reformer RF1 being fed with water H2O. The water passes the first reformer RF1 and is heated by the reforming process. Said first part PF1 of the feed stream FDS in this example is not compressed by a supersonic compressor SCO but by a low pressure compressor CLP and a subsequently arranged high pressure compressor CHP—both being driven by a turbine TRB being supplied with a driving fluid DRF.

Figure 5:
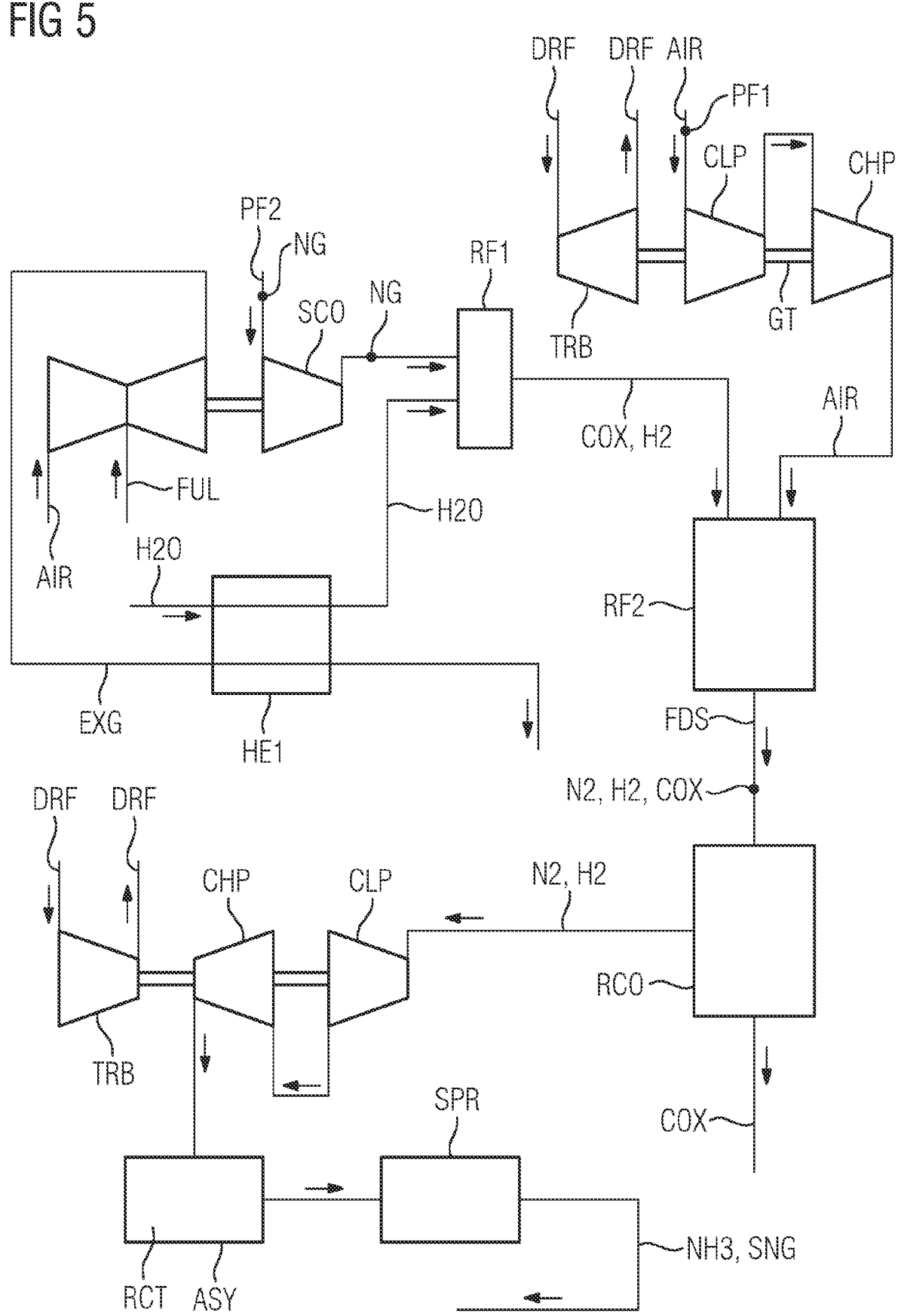

Another variant of the ammonia NH3 synthesis shows FIG. 4. In this example only the first part PF1 of the feed stream FDS respectively the air AIR is compressed by a supersonic compressor SCO. A second part PF2 of the feed stream FDS respectively the natural gas NG is compressed by an ordinary centrifugal compressor CO. Both compressors SCO, CO are driven by a drive unit DRV respectively a gas turbine GT being supplied with air AIR and fuel FUL. An additional stream of air extracted from the output of the supersonic compressor SCO compressing the air AIR is used as additional gas turbine feed GTF. This hot compressed air AIR improves the GT overall efficiency. Exhaust gas EXG of the gas turbine GT is used to heat the first part PF1 of the feed stream FDS. Downstream the process of FIG. 4 is basically the same as illustrated in FIGS. 2 and 5.

FIG. 3 shows a schematic flow diagram of a propane dehydrogenation process using features of the invention. A first part PF1 of the process fluid respectively the feed stream FDS is air AIR being compressed by a supersonic compressor SCO according to the invention. A second part PF2 of the feed stream FDS is propane C3H8. The exhaust gas of the gas turbine GT is driving a supersonic compressor SCO. The exhaust gas EXG of the gas turbine GT generated from a stream of air AIR and fuel FUL supplies heat to a second heat exchanger HE2. A The first part PF1 of the feed stream being heated during compression in the supersonic compressor SCO. The second part PF2 of the feed stream FDS respectively the propane C3H8 is heated in the second heat exchanger HE2 for entering at a temperature of approximately 600° C. a reactor RCT together with the first part PF1 of the feed stream FDS respectively the compressed air AIR. Output of the reactor is on the one hand exhaust gas EXG and on the other hand a deactivated catalyst DAC of the reaction. Said exhaust gas EXG of the reactor RCT contains hydrogen N2, oxygen O2 and carbon oxide COX, CO, CO2. The other output of the reactor RCT is the gas product SNG propylene C3H6. To use the high temperature level of the gas product SNG said propylene C2H6 is passed through the second heat exchanger HE2 to heat the second part PF2 of the feed stream FDS. The gas-product SNG is dried in a dryer DRY and separated from impurities in a separator SPT.

The invention claimed is:

1. A method for generating a gas-product (SNG), comprising:
a) providing a first part (PF1) of a feed stream (FDS),
b) providing a second part (PF2) of a feed stream (FDS),
c) combining said first part (PF1) of said feed stream (FDS) with said second part (PF2) of said feed stream (FDS) into said feed stream (FDS),
d) heating at least one of
  i. said first part (PF1) of said feed stream (FDS),
  ii. said second part (PF2) of said feed stream (FDS) before step c),
  iii. said feed stream (FDS) after step c),
e) conducting the feed stream (FDS) into a reactor (RCT),
f) reacting the feed stream (FDS) into the gas-product (SNG), wherein step d) is as least partly performed by compressing the respective stream (FDS) by a supersonic compressor (SCO) such that the respective stream is heated.

2. The method according to claim 1,
wherein said first part (PF1) of said feed stream (FDS) is heated by compressing by a supersonic compressor (SCO) according to step d).

3. The method according to claim 1,
wherein said second part (PF2) of said feed stream (FDS) is heated upstream of entering the reactor (RCT) by exchanging heat with the reactor (RCT) and/or with the gas-product (SNG) downstream of exiting the reactor (RCT).

4. The method according to claim 1,
wherein said supersonic compressor (SCO) is driven by a gas turbine (GT) generating exhaust gas (EXG), and
wherein said exhaust gas (EXG) is used to heat said second part (PF2) of said feed stream (FDS).

5. The method according to claim 1,
wherein said first part (PF1) of said feed stream (FDS) essentially consists of hydrocarbon (CH4),
wherein said second part (PF2) of said feed stream (FDS) essentially consists of water (H2O), and
wherein the gas-product (SNG) essentially consists of syngas (SYG).

6. The method according to claim 5,
wherein said syngas (SYG) is separated from water (H2O) and from carbon-oxide (COX) to obtain hydrogen (H2) downstream of the reactor (RCT).

7. The method according to claim 1,
wherein said first part (PF1) of said feed stream (FDS) essentially consists of air (AIR),
wherein said second part (PF2) of said feed stream (FDS) essentially consists of propane (C3H8), and
wherein said gas-product (SNG) essentially consists of propylene (C3H6).

8. The method according to claim 7,
wherein said first part (PF1) of said feed stream (FDS) is heated by compressing by a supersonic compressor (SCO) according to step d).

9. The method according to claim 7,
wherein said second part (PF2) of said feed stream (FDS) is heated upstream of entering the reactor (RCT) by exchanging heat with said first part (PF1) of said feed stream (FDS) downstream of exiting said supersonic compressor (SCO).

10. The method according to claim 1,
wherein said first part (PF1) of said feed stream (FDS) essentially consists of syngas (SYG),
wherein said second part (PF2) of said feed stream (FDS) essentially consists of air (AIR), and
wherein said gas-product (SNG) essentially consists of ammonia (NH3).

* * * * *